United States Patent [19]

Cohen

[11] Patent Number: 5,686,639

[45] Date of Patent: Nov. 11, 1997

[54] QUINONE DIIMMONIUM SALTS AND THEIR USE TO CURE EPOXIES

[75] Inventor: Murray S. Cohen, Morristown, N.J.

[73] Assignee: Epolin, Inc., Newark, N.J.

[21] Appl. No.: 425,430

[22] Filed: Apr. 20, 1995

[51] Int. Cl.$^6$ .............. C07F 9/66; C07C 205/00; C07C 207/00
[52] U.S. Cl. .............. 556/33; 558/411; 524/305; 524/307
[58] Field of Search .............. 556/33; 524/305, 524/307; 558/411

[56] References Cited

U.S. PATENT DOCUMENTS

| | | | |
|---|---|---|---|
| 3,341,464 | 9/1967 | Susi et al. | 252/300 |
| 3,440,257 | 4/1969 | Susi et al. | 260/440 |
| 3,484,467 | 12/1969 | Susi et al. | 260/440 |
| 3,575,871 | 4/1971 | Susi et al. | 252/300 |
| 3,631,147 | 12/1971 | Susi | 260/45.75 R |
| 3,637,769 | 1/1972 | Susi | 260/396 N |
| 3,670,025 | 6/1972 | Susi et al. | 260/576 |
| 3,962,290 | 6/1976 | Grosso | 260/396 |
| 4,231,950 | 11/1980 | Idelson | 556/33 |
| 4,791,023 | 12/1988 | Suzuki et al. | 556/33 X |
| 4,937,338 | 6/1990 | Flohr et al. | 556/33 X |
| 5,501,724 | 3/1996 | Loff | 106/10 |

*Primary Examiner*—Paul F. Shaver
*Attorney, Agent, or Firm*—Roberts & Mercanti, LLP

[57] ABSTRACT

The invention relates to divalent immonium salts which are near infrared dyes of the formula (I).

$$(R_2NAr)_2-N^+=Ar'=N^+R_2+2X^- \quad (I)$$

wherein:

R=$C_1$ to $C_6$ alkyl; Ar=divalent phenyl which may or may not be ring substituted with one or more alkyl, alkoxy, halogen, nitro, cyano or carboalkoxy groups; Ar'=quinoidal phenyl which may or may not be ring substituted with one or more alkyl, alkoxy, halogen, nitro, cyano or carboalkoxy groups; and X=an anion of a strong acid. A double charged dye cation having an $SbF_6$ anion associated with the dye can act both a near IR dye and an epoxy curative.

6 Claims, No Drawings

QUINONE DIIMMONIUM SALTS AND THEIR USE TO CURE EPOXIES

FIELD OF THE INVENTION

The present invention relates to compounds which are near infrared dyes. More particularly, the invention relates to a new class of near infrared absorbers that can be used with a wide variety of plastics as additives where they absorb infrared radiation. Some of these dyes additionally find use as epoxy curing agents. In the latter case, the invention provides transparent, heat stable, adherent epoxy coatings and interface bonding adhesives containing near infrared dyes. These can be applied to glass, metal or other non-porous surfaces for the purpose of depositing a coating on these surfaces or to bond two similar or dissimilar surfaces together.

DESCRIPTION OF RELATED PRIOR ART

Near IR dyes are well known in the art as exemplified by U.S. Pat. Nos. 3,341,464; 3,440,257; 3,484,467; 3,575,871; and 3,670,025, which are incorporated herein by reference. In general these dyes have the property of passing light in the visible portion of the spectrum (450 to 700 nanometers) and absorbing strongly in the near IR portion of the spectrum (700 to 1500 nanometers). By their use, it is possible to sequester about 35 to 50 percent of the sun's total energy. The amount is much higher when absorbing radiation from tungsten filament lamps. These dyes can be incorporated in a variety of plastics and can be used as sunglasses, welding shields, laser protection eyewear, windows, television filters, projection lenses and other products which can attenuate the heat from radiant sources or absorb specific laser radiation. As described in the referenced patents, the dye is incorporated into plastic film or sheet by molding the plastic with the dye, imbibing the dye into the preformed plastic sheet or by forming the sheet by cell casting and polymerizing the polymerizable monomer containing the dissolved dye. U.S. Pat. Nos. 3,440,257 and 3,341,464 disclose monovalent dye salts. In contrast, the dyes of this invention are divalent salts and possess optical properties that differ from those revealed in the prior art.

The invention provides a class of N,N-dialkyl-N',N'-bis dialkylaminophenyl-p-benzoquinone diimmonium salts shown to be useful near infrared absorbers. They are obtained by the double oxidation of the corresponding tris-p-dialkyl aminophenyl amines. The dyes of this invention are of use in maximizing the frequency range of absorption while at the same time allowing transmission in the visible range to be as transparent as possible. In general, it has been found that the dicationic dyes are not sharp absorbers but tend to absorb over a broader band of frequencies and to extend the absorption to lower wave lengths. Of more practical importance is the fact that the dicationic dyes have greater absorbency at their absorption maximum in the near IR. This means that the same concentration of dye can reduce transmission at selected wave lengths by a greater amount than the corresponding monocationic dye. These become important considerations when designing glazing or automobile heat shields. By extending the absorption down to the upper end of visible frequencies and at a lower concentration of dye, it is possible to remove a larger proportion of the near IR. This is particularly desirable if two dyes are used together. In such a case one dye extends down to the upper limits of the visible range (650 manometers) while the second dye captures the longer wave lengths (1200 to 1500 nanometers).

It is known in the art that monovalent near IR dyes cannot be used to cure epoxies because they either inhibit the cure of the epoxy or they are attacked by the conventional curing agents used to cure epoxies, and in the process are destroyed and/or lose their effective near IR absorbance. It has now been found that if certain requirements are met in the molecular structure of the near IR dye, that it is possible to achieve a suitable cure or chain extension and cross-linking of a epoxy continuous phase. A good cure can be achieved with the divalent dyes of this invention which have an $SbF_6$ anion.

The above referenced patents do not disclose the use of near IR dyes in epoxy coatings or adhesives because those dyes are found to react with epoxy curatives. When this happens the epoxy either fails to harden or the curative attacks the dye and bleaches it so that it loses its absorbance in the near IR range. Dyes that contain singly charged cations do not cure epoxides. It has now been found that certain divalent near IR dyes may be used in an epoxy coating to form a tenacious film on glass or other impermeable surfaces such as metals or ceramics. Useful epoxy coatings incorporating near IR dyes have been found to be feasible by selecting specific near IR dyes or combinations of dyes. The correct combination of dye and epoxy performs two functions. First, it maintains its absorbance of the near IR portion of the spectrum. Second, the dye itself acts as a curative for the epoxy. U.S. Pat. Nos. 3,637,769 and 3,962,290 describe divalent cations that do cure epoxies but in neither patent is there any reference to the use of dyes in epoxies. A wide range of polymeric substrates are cited as useful carriers of the dyes but in no instance are epoxies mentioned. All of the above patents are incorporated herein by reference.

The value of epoxy coatings and adhesives on non-porous surfaces or the bonding together of two non-porous surfaces is apparent in that these hard surfaces are required in applications where plastic or soft surfaces would abrade and lose their ability to perform. For example, two pieces of glass glazing can be bonded together with epoxy containing a near IR dye. The glazing can then function as a heat shield by reducing the transfer of heat from the sun. At the same time the glazing would maintain the high abrasion resistance of glass. Similarly, bonded glass lenses can be used as protective eyewear wherein the epoxy-dye bond serves to absorb powerful frequencies of laser light, such as that emitted by the neodymium YAG laser, but also can act to eliminate shattering of the lens on impact. Unlike the lenses used for laser protection which are made of high strength polycarbonate, glass lenses would be far more resistant to abrasion. When the dyes are used as coatings on plastics or milled into plastics they become excellent absorbers of near IR radiation and are suitable for use in welder goggles, sun glasses, fire protection, shields for fire fighters and other shielding applications. They provide particularly good transmission in the visible portion of the spectrum but are highly efficient absorbers above about 700 nanometers which is the frequency range responsible for most radiant heating. Thus they have value as heat shields for glazing for buildings and automobile windshields. The ability to bond two pieces of glass together with a film containing the dye or with epoxy cured with the dye makes them useful as scratch-resistant safety windshields.

It has been found that the presence of a double charged cation itself, is not sufficient to cause the curing of the epoxy oligomer. A second factor is required for successful cure and that is the anion associated with the dye must be $SbF6$. As an example of this specificity it has been found that the doubly charged dye that has a $PF_6$ or $AsF_6$ anion will not cure epoxy oligomers but the $SbF_6$ anion on the same cationic nucleus would do so. By proper selection it is also possible to effect epoxy cures with singly charged cations as long as there is a critical concentration of the doubly charged $SbF_6$ ion present. In most cases this is a desirable feature in an overall composition because the combination of two or more dyes allows the final coating to absorb a greater frequency range in the near IR. The divalent diimmonium salts of this invention are unique in that they allow transmission of a significant fraction of visible light in the 450 to 700 nanometer range. By dissolving these dyes in liquid epoxies it is possible to coat glass or other surfaces and achieve a good cure of the epoxy under conventional thermal cure conditions. With glass, this forms an adherent shield which transmits visible light but strongly absorbs the near IR portion of the spectrum. When coated on polished metals, the coating absorbs near IR and reflects the visible light. In both cases, as coatings on transparent surfaces or on mirrored surfaces, there are numerous applications for their use. In addition the epoxy can be used as a bonding agent to seal together glass or glass on metallic mirror surfaces. Both approaches make use of the hard, abrasion resistance of glass while the epoxy-dye interface functions as a near IR filter and absorber. The epoxy formulations containing near infrared dyes of this invention with $SbF_6$ anions are thermally curable by conventional curing techniques.

SUMMARY OF THE INVENTION

The invention provides a near IR dye of the formula I:

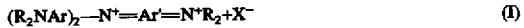  (I)

wherein:

$R=C_1$ to $C_6$ alkyl;

Ar=divalent phenyl which may or may not be ring substituted with one or more alkyl, alkoxy, halogen, nitro, cyano or carboalkoxy groups;

Ar'=quinoidal phenyl which may or may not be ring substituted with one or more alkyl, alkoxy, halogen, nitro, cyano or carboalkoxy groups; and X=an anion of a strong acid.

The invention also provides a method of preparing compounds of the formula (I) by double oxidizing a compound of the formula II:

  (II)

The invention also provides a near IR dye compound of the formula IV:

  (IV)

and a near IR dye of the formula:

The invention still further provides a admixture of an epoxide containing monomer or oligomer, and a near IR dye agent of formula I wherein $X=SbF_6$ as well as the resulting cured composition and curing process.

DETAILED DESCRIPTION OF THE PREFERRED EMBODIMENT

The invention provides a near IR dye of the formula I:

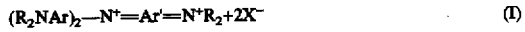  (I)

wherein:

$R=C_1$ to $C_6$ alkyl;

Ar=divalent phenyl which may or may not be ring substituted with one or more alkyl, alkoxy, halogen, nitro, cyano or carboalkoxy groups;

Ar'=quinoidal phenyl which may or may not be ring substituted with one or more alkyl, alkoxy, halogen, nitro, cyano or carboalkoxy groups; and X=an anion of a strong acid and preferably is a tetrafluoroborate, hexafluoroarsenate, hexafluorophosphate, hexafluoroaluminate, hexafluorosilicate, hexafluoroantimonate or perchlorate.

All of the compounds represented by I are near IR dyes in that they absorb electromagnetic radiation in the range of 720 nanometers to 1500 nanometers. Any of the above compounds may be blended with polymers such as those enumerated hereinafter to form IR absorbing compositions. The compounds of formula I may be prepared by the double oxidation of the neutral amines of formula II,

  (II)

wherein R and Ar have the same values as shown in formula I. The double oxidizing is conducted with an oxidant having the formula MZ or $MZ_2$ wherein M is silver or copper and Z is an anion selected from the group consisting of nitrate, chloride, bromide, sulfate and acetate. The oxidant, when present in stoichometric amount, will oxidize the neutral amine II to the near IR dye I. This is illustrated by the oxidation of II with $AgNO_3$ and $CuBr_2$ in equations A and B:

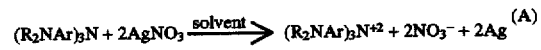  (A)

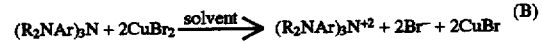  (B)

The nitrate and bromide, or other organic salt made directly in this oxidation is not isolated, rather, it is converted in situ, to the more stable salt of a strong acid. This is illustrated in the following equations C and D which show the formation of I.

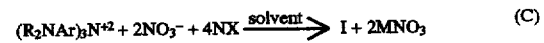  (C)

or

  (D)

The NX salt used in approximately twice the stoichometric amount, where N is potassium or sodium and the X anion is the same as shown in I. The oxidation and metathasis reactions shown in equations A, B, C and D are carried out in an organic solvent in which the neutral amine base and the oxidant are at least partially soluble. The copper salts used in the oxidation are selected from a wide variety which include the chloride, bromide, sulfate and acetate. The silver salts include the nitrate and acetate. Cupric chloride, cupric bromide, cupric sulfate and cupric nitrate are particularly preferred. Useful silver salts include silver nitrate although any cupric or silver salt which is soluble to an appreciable extent in the organic solvent may be used in the oxidation reaction. The solvent used is not critical provided it is inert to the reactants and the product under the reaction conditions. Acetone is a preferred solvent due to its ease of handling, however, other solvents, such as dimethylformamide, dimethylacetamide and tetrahydrofuran also give good results. The amount of the cupric salt used in the oxidation reaction is approximately two moles per mole of the amine. The reaction temperatures used in the oxidation are not critical. Ordinarily, temperatures from about 20° C. to about 50° C. are used. Generally, following completion of the oxidation, insoluble inorganic salts are filtered off and the product isolated from solution by cooling or by precipitation from solution with water. The solid product is then filtered off, washed free of solvent and residual salts and dried, according to standard techniques. The amount of oxidant used in the oxidation reaction is approximately two moles per mole of amine. The reaction temperatures for the oxidation are not critical.

Ordinarily, temperatures from about 20° C. to about 50° C. are satisfactory. Generally, following completion of the oxidation, insoluble inorganic salts, and, in the case of silver salt oxidation, metallic silver, is removed by filtration. The product is isolated from solution by cooling and by the addition of a non-solvent or water to the water miscible solvent. The solid product that separates is collected by filtration, washed free of solvents as well as residual water soluble inorganic salts and dried according to standard techniques. The compounds illustrated by formula I possess unique properties. They have many of the same properties described in earlier patents for near infrared dyes such as those claimed in U.S. Pat. Nos. 3,440,257; 3,484,467; 3,575,871; 3,341,464; 3,670,025 and 3,709,830. All of the dyes described in these patents absorb radiant energy in the near infrared portion of the spectrum but they differ from the dyes illustrated by formula I in that they absorb at higher wavelengths. Thus a critical region of the spectrum, from approximately 700 nanometers to about 900 nanometers, can now be absorbed by the use of near IR dyes described herein. There has been reported in prior art other dyes that were prepared by the single oxidation of the neutral amines of formula II. This is illustrated in formula III.

wherein R and X=the same as described for formula I.

Of particular interest with respect to this disclosure is the discovery that the class of compounds described in U.S. Pat. Nos. 3,341,464 and 3,440,257 can also be used as precursors to make products of this invention. Thus, the single oxidation of III by the same reagents which are used to oxidize the basic neutral amine II, can give excellent yields of I as illustrated in equations E and F using silver nitrate as oxidant and sodium hexafluoroantimonate as the metathesis reagent.

wherein X=SbF$_6$, PF$_6$, or any other anion derived from a strong acid. In the case illustrated above, I is the SbF$_6^-$ salt. Hexafluorophosphate salts have special utility because of their solubility, melting point and other physical property characteristics. They are illustrated by formula IV

wherein R and Ar are the same shown for I.

The singly oxidized near infrared dyes are described in prior art and show significant differences from the doubly oxidized dyes of this invention. The doubly oxidized dyes absorb over a much broader frequency range. In addition, their absorption extends down into the lower frequencies.

The doubly oxidized dyes of structure I which are SbF$_6^-$ salts, have the additional property of acting as curatives for epoxy oligomers. This is a completely unexpected property. Although all the prior art cited in the aforementioned patents stress the use of near IR dyes in plastic matrices, they do not teach that they can be used in epoxy compositions. It has now been shown that such epoxy-dye combinations can form tenacious hard films on glass or other impermeable surfaces such as metals and ceramics.

The correct combination of dye and epoxy performs two functions. First, it maintains its absorbency of the near IR portion of the spectrum. Second, the dye itself acts as a curative for the epoxy. U.S. Pat. Nos. 3,637,769 and 3,962,290 describe divalent cations that can cure epoxies, but they do so slowly and incompletely. Neither patent teaches their use in epoxies. For example, a wide range of polymeric substances of specific type are cited as useful carriers of the dyes, yet, in no instance, are epoxies specified.

The epoxide containing monomer or oligomer may be any compound having a reactive oxirane structure. The most preferred of these are bisphenol epoxy compounds such as diglycidylethers of bisphenols, triglycidyl isocyanurates available as Araldite PT810 from Ciba-Geigy, hydantoin epoxies available as Aracast hydantoin resins from Ciba Geigy, epoxy phenol novolac resins available as Epoxy Resin XB 3337 from Ciba Geigy and D.E.N. 431, 438 and 439 from Dow Chemical Company, epoxy cresol novolac resins available as ECN 1235, 1273 and 1299 from Ciba Geigy, liquid epoxy resins 333,334 and 335 available from Dow Chemical, and Epon Resins 1004F, 813, 815, 823, 8132, 8201, 826, 828, 829, 829H, 830, 8280 and 8281 available from Shell Chemical Corporation.

In the above admixture, the dye curing agent is present in an amount sufficient to cure the epoxide monomer or oligomer and is preferably present in an amount of from about 0.15% to about 5% by weight of the epoxide monomer or oligomer, more preferably from about 0.25 % to about 2% and most preferably from about 0.25 to about 1%. The maximum amount is that amount which would be soluble in the epoxide monomer or oligomer.

The admixture may be cured by heating the admixture to a temperature of from about 100° C. to about 130° C., or more preferably from about 120° C. to about 130° C., for from about 60 to about 180 minutes. The result is a cured, near infrared absorbing composition which comprises the reaction product of the epoxide containing monomer or oligomer with the near IR curing agent.

In an alternative embodiment, the cured, near infrared absorbing composition may further contain an additional near IR dye which absorbs radiation in the 700 nm to 1500 nm range and transmits radiation in the 450 to 700 nm range. Such are well known in the art and examples of which are mentioned in the above U.S. patents. Such additional dye may be used to tailor a composition having a very specific light absorption. Such an additional dye, when one is used is preferably present in an amount of from about 0.15% to about 5% by weight of the epoxide monomer or oligomer, more preferably from about 0.25 % to about 2% and most preferably from about 0.25 % to about 1%. The maximum amount is that amount which would be soluble in the epoxide monomer or oligomer.

In another alternative embodiment, the near infrared absorbing composition may further be blended with other transparent polymers which transmits radiation in the 450 to 1500 nm range. Such are well known in the art and examples of which are mentioned in the above U.S. patents. Such additional polymer, when one is used is preferably present in an amount of from about 99.0% to about 99.999% by weight of the solid parts of the overall composition, more preferably from about 99.2% to about 99.9%. Examples of such polymers non-exclusively include, any of those hereinafter mentioned as suitable for use as a substrate. The mixture may be formed in any suitable, substantially inert solvent which does not react with or adversely affect the mixture components. Such non-exclusively include nitropropane, tetrahydrofuran, gamma butyrolactone, glycol ethers such as propylene glycol monomethyl ether and methyl cellosolve, alcohols such as ethanol and n-propanol, ketones such as methyl ethyl ketone, ethers and esters. The solvent facilitates opening the polymer surface and allowing the dye to penetrate the substrate after which the solvent is allowed to evaporate. The blended composition may be coated on a suitable substrate to form an article or be applied between two substrates of similar or dissimilar materials as an adhesive.

Various organic plastic substrates are available having suitable transmission properties in the visible region. Illustrative examples includes cellulose derivatives such as cellulose nitrate, cellulose acetate, regenerated cellulose and cellulose ethers such as ethyl and methyl cellulose; polystyrene plastics such as polystyrene per se and polymers and copolymers of various ring substituted styrenes, for example o-, m- and p-methylstyrene and other ring-substituted styrenes as well as side-chain substituted styrenes such as alpha-, methyl- and ethylstyrene and various other polymerizable and copolymerizable vinylidenes; various vinyl polymers and copolymers such as polyvinyl butyral and other acetals, polyvinyl chloride, polyvinyl acetate and its hydrolysis products, polyvinyl chloride-acetate copolymers; acrylic resins such as polymers and copolymers of methyl acrylate, methyl methacrylate, acrylamide, methylolacrylamide and acrylonitrile; polyesters and unsaturated-modified polyester resins such as those made by condensation of polycarboxylic acids with polyhydric phenols or modified using unsaturated carboxylic acid and further modified by reacting the alkyd with another monomer; polymers of allyl diglycol carbonate and various copolymers using as a crosslinking monomer an allyl ester of various acids. Particularly preferred substrates are cellulose acetate, methyl methacrylate, polystyrenes and polymers of allyl diglycol carbonates. The dyes may be blended with the solid polymers and extruded or molded. They may be dissolved in a solution of the polymer and form a coating on a suitable substrate when the solvent evaporates.

The following non-limiting examples serve to illustrate the invention. All percentages are by weight and temperatures are in degrees of Celsius. All samples are prepared by dissolving the dye in an epoxy oligomer or first, in a volatile, unreactive solvent such as nitropropane or tetrahydrofuran and then mixing the dye solution with epoxy oligomer. The surface of glass is then coated with the epoxy-dye-solvent system and the solvent is allowed to evaporate at 100° C. for one-half hour. The cure is then effected at 130° C. to 145° C. over 3 hours.

To illustrate the unique properties of the +2 dyes associated with various anions, a comparison is made of +1 and +2 dyes of formula I with related near IR dyes described in the above prior patents. These are built around the basic molecule represented by formula V.

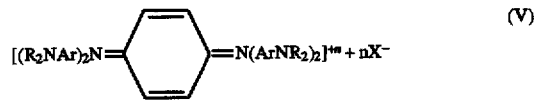

where R, Ar and X have the same values as shown in I and n=1 or 2.

EXAMPLE 1

To illustrate the difference between monovalent (+1) and divalent (+2) $SbF_6$ dyes with respect to their ability to cure an epoxy oligomer, in this case Shell 828, the performance of $SbF_6$ dyes is compared.

| TYPE | CATIONIC CHARGE +1 or +2 | STRUCTURE R | DYE CONC. (%) | RESULTS AFTER 3 Hr. Cure @ 130° C. |
|---|---|---|---|---|
| III | +1 | n-$C_4H_9$ | 1.3 | NO CURE |
| V | +2 | n-$C_4H_9$ | 1.0 | FULL CURE |
| V | +1 | n-$C_4H_9$ | 0.2 | NO CURE |
| I | +2 | n-$C_4H_9$ | 0.3 | FULL CURE |
| I | +2 | $C_2H_5$ | 2.4 | FULL CURE |
| III | +1 | $C_2H_5$ | 3.0 | NO CURE |

EXAMPLE 2

The ability of a divalent (+2) cationic salt containing $SbF_6$ to cure a typical oligomer (Shell 828) is compared with other divalent cationic salts containing other anions.

| TYPE | CATIONIC CHARGE +1 or +2 | ANION | STRUCTURE R | DYE CONC (%) | RESULTS AFTER 3 HR. CURE @ 130° C. |
|---|---|---|---|---|---|
| V | +2 | $PF_6$ | n-$C_4H_9$ | 0.3 | NO CURE |
| I | +2 | $PF_6$ | n-$C_4H_9$ | 0.3 | NO CURE |
| I | +2 | $SbF_6$ | n-$C_4H_9$ | 0.3 | FULL CURE |
| I | +2 | $PF_6$ | $C_2H_5$ | 0.3 | NO CURE |
| I | +2 | $AsF_6$ | n-$C_4H_9$ | 0.3 | NO CURE |
| V | +2 | $SbF_6$ | n-$C_4H_9$ | 0.3 | FULL CURE |

EXAMPLE 3

The presence of an $SbF_6$ divalent (+2) cationic dye allows the cure of various epoxy oligomers containing monovalent dyes.

| TYPE | CATIONIC CHARGE | ANION | STRUCTURE R | DYE CONC (%) | EPOXY* TYPE | RESULTS AFTER 3 HR. CURE @ 130° C. |
|---|---|---|---|---|---|---|
| V | +2 | $SbF_6$ | n-$C_4H_9$ | 0.15 | 828 | } SOFT CURE |
| V | +1 | $SbF_6$ | n-$C_4H_9$ | 0.15 | 828 | |
| I | +2 | $SbF_6$ | n-$C_4H_9$ | 0.50 | 1510 | } FULL CURE |

-continued

| TYPE | CATIONIC CHARGE | ANION | STRUCTURE R | DYE CONC (%) | EPOXY* TYPE | RESULTS AFTER 3 HR. CURE @ 130° C. |
|---|---|---|---|---|---|---|
| V | +1 | $SbF_6$ | $n-C_4H_9$ | 0.25 | 1510 | |
| I | +2 | $SbF_6$ | $n-C_4H_9$ | 0.85 | 828 | } FULL CURE |
| V | 12 | $SbF_6$ | $n-C_4H_9$ | 0.85 | 828 | |
| I | +2 | $SbF_6$ | $C_2H_5$ | 0.80 | 1510 | } NO CURE |
| I | +1 | $SbF_6$ | $C_2H_5$ | 0.80 | 1510 | |
| V | +2 | $AsF_6$ | $C_4H_9$ | 0.80 | 1510 | } NO CURE |
| I | +1 | $AsF_6$ | $C_4H_9$ | 0.80 | 1510 | |
| I | +2 | $PF_6$ | $nC_4H_9$ | 0.80 | 1510 | } NO CURE |
| V | +1 | $SbF_6$ | $nC_4H_9$ | 0.80 | 1510 | |

*These are Shell Chemical Company epoxy oligomer products.

EXAMPLE 4

Conventional curing agents used for epoxy curing either fail when IR dyes are present or else the curatives attack and decolorize the dye.

| TYPE | CATIONIC CHARGE | ANION | STRUC- TURE R | DYE CONC (%) | CURA- TIVE TYPE & CONC. (%) | RESULTS AFTER 3 HR. CURE @ 130° C. |
|---|---|---|---|---|---|---|
| V | +2 | $SbF_6$ | $n-C_4H_9$ | 0.3 | CATI- ONIC (0.2) | NO CURE |
| V | +2 | $SbF_6$ | $n-C_4H_9$ | 0.3 | AMINE (10.0) | NO CURE |
| V | +2 | $PF_6$ | $n-C_4H_9$ | 0.3 | ANHY- DRIDE (20.0) | CURED BUT DE- COLOR- IZED |

EXAMPLE 5

N,N-di-n-butyl-N,N'-bis(di-n-butylaminophenyl)-p-benzoquinone-diimmonium hexafluorophosphate

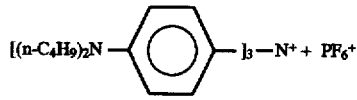

(a) From the Free Base

To 25.0 g of tris-p-N-N-dibutylaminophenyl amine (0.04 mole) dissolved in 100 ml of tetrahydrofuran there is added with stirring, 29.4 g (0.175 mole) of potassium hexafluorophosphate and 13.6 g of silver nitrate dissolved in 45 ml of distilled water. Warm to 40° to 45° C. for 2.0 hours and add 150 ml of acetone to dissolve the solids that form. Filter off the insolubles and wash them with 30 ml of warm acetone. The filtrate is then added to 250 ml of distilled water to give a green precipitate that crystallizes on standing. This is removed by filtration, washed with 150 ml distilled water and dried. The product weights 32.0 g (73% of theory). A sample dissolved in methyl ethyl ketone and precipitated with heptane melted at 173°–174° C.

Theory for $C_{42}H_{66}N_4P_2F_{12}$

| (%) | C | H | N |
|---|---|---|---|
| Theory | 55.03 | 7.21 | 6.11 |
| Found | 55.07 | 7.51 | 6.16 |

(b) From the Monovalent Salt

1. Preparation of Monovalent Salt Tris-(p-di-n-Butylaminophenyl) aminium hexafluorophosphate

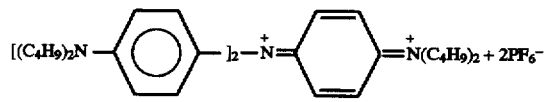

To 25.0 g of tris-p-N-N-dibutylaminophenyl amine (0.04 mole) dissolved in 75 ml of acetone, there is added, 14.7 g (0.087 mole) of potassium hexafluorophosphate and 6.8 g (0.04 mole) of silver nitrate suspended in 100 ml of acetone. The precipitation of metallic silver occurs almost immediately. The solution is warmed to 45° C. for 2.0 hours and the mixture filtered to remove the precipitated silver. The filter is washed with 20 ml of acetone which is combined with the filtrate. The filtrate is added to 250 ml of distilled water with good stirring to give a green precipitate that solidifies on standing. The solids are collected on a filter, washed with water and dried. It weighs 29 g (94% of theory).

Theory for $C_{42}H_{66}N_4PF_6$

| (%) | C | H | N |
|---|---|---|---|
| Theory | 65.37 | 8.56 | 7.26 |
| Found | 65.24 | 8.66 | 7.28 |

2. Conversion Of Monovalent Salt To Divalent Salt 12.0 g (0.02 mole) of tris-dibutylaminophenyl aminium hexafluorophosphate is dissolved in 200 ml of tetrahydrofuran. A slurry of 3.4 g (0.02 mole) of silver nitrate and 7.2 g (0.04 mole) of potassium hexafluorophosphate in 100 ml of THF is added with stirring. The reaction is heated at 50° C. for 2.0 hours and filtered. To the filtrate is added 200 ml of distilled water. The precipitated green solid is removed by filtration. It can be re-crystallized from tetrahydrofuran to give a green crystalline solid, 12.7 g (85% of theoretical yield) m.p. 174°–175° C.

EXAMPLE 6

N,N-diethyl-N',N'-bis(diethylaminophenyl)-p-benzoquinone diimmonium hexafluorophosphate

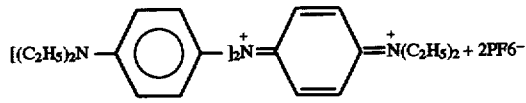

(a) From a Free Base

To 9.14 g (0.02 mole) of tris-p-diethylaminophenylamine dissolved in 200 ml of tetrahydrofuran there is added, with stirring, 6.8 g (0.04 mole) of silver nitrate and 14.42 g (0.08 mole) of potassium hexafluorophosphate. After 2 hours the solution is filtered to remove the precipitated silver and potassium nitrate. To the filtrate 200 ml of water is added. A crystalline solid separates, is filtered and washed with 100 ml water. The product weights 12.5 g (83.6% of theory). A crystallized sample from acetone-heptane washed with ethyl acetate has a m.p. 151.5°–154° C.

Theory for $C_{30}H_{42}N_4F_{12}P_2$:
Theory %C=48.01; %H—5.62; %N=7.49; %F=30.48
Found %C=46.91; %H=5.90; %N=7.36; %F—29.50

(b) From the Monovalent Salt:

1. Preparation Of Monovalent Salt

To 9.14 g (0.02 mole) of tris-p-diethylaminophenylamine dissolved in 200 ml of acetone there is added, with stirring, 3.4 g (0.02 mole) of silver nitrate and 7.2 g (0.04 mole) of potassium hexafluorophosphate. After 2 hours at 50° C. the solids are removed by filtration, washed with 150 ml of distilled water. The green solid that separates is collected on a filter and washed with water. The product weights 10.2 g (88% of theory) that melts at 103.5°–104.5° C.

Theory for $C_{30}H_{42}N_4F_6P$:
Theory %C=59.70; %H=6.97; %N=9.29
Found %C=88.37; %H=7.22; %N=10.01

2. Conversion Of Monovalent Salt To Divalent Salt 12.4 g (0.02 mole) of tris [p-diethylaminophenyl] aminium hexafluorophosphate dissolved in 150 ml of acetone there is added, with stirring, 3.4 g (0.02 mole) of silver nitrate and 7.2 g (0.04 mole) of potassium hexafluorophosphate in 100 ml of acetone. The reaction mixture is heated with stirring at 50° C. for 2.5 hours. Filtration removes the precipitated silver metal. This is washed with 50 ml of acetone and the combined filtrate is treated with 200 ml of distilled water. The precipitated green solid is separated on a filter, washed with water and dried. It weighs 13.0 g (85% of theory) melting at 151°–153° C.

EXAMPLE 7

N,N-di-n-butyl-N',N'-bis(di-n-butylaminophenyl)-P-benzoquinone diimmonium hexafluoroantimonate

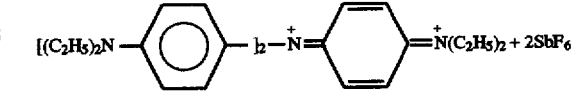

(a) From a Free Base

A solution was prepared of tris p-di-n-butylaminophenylamine, 300 g (0.479 mole) in 1 liter of acetone. To this is added 162 g (0.96 mole) of silver nitrate and 495 g (1.92 mole) of sodium hexafluoroantimonate with good stirring. The mixture is stirred at 40°–45° C. overnight, cooled and the silver removed by filtration. Add to the filtrate 2 liters of distilled water. The product separates as an oil which is washed with 2×500 ml of water. It solidifies after standing overnight. The solids are removed by filtration and added to hot isopropanol and filtered. The insoluble portion, when dried, weighs 473 g (90% of theory). A sample re-crystallized from tetrahydrofuran and heptane had a m.p. of 193°–195° C.

Theory for $C_{43}H_{66}N_4Sb_2F_{12}$:
Theory %C=45.92; %H—6.01; %N=5.10; %F—20.77
Found %C=46.04; %H=6.06; %N=5.02; %F=21.08

(b) From the Monovalent Salt:

1. Preparation Of Monovalent Salt

A solution was prepared of 30.0 g (0.05 mole) of tris p-di-n-butylaminophenyl amine in 100 ml of acetone. A mixture of 8.1 g (0.05 mole) of silver nitrate and 25.8 g (0.10 mole) of sodium hexafluoroantimonate in 100 ml of acetone is added. The mixture was stirred at 40°–45° C. for 3 hours and the precipitated silver metal removed by filtration. Add to the filtrate and washings 200 ml of distilled water. A heavy oil precipitates which solidifies on standing. This is collected on a filter, washed with water and dried. A sample is re-crystallized out of hot isopropanol to give green crystals, 29.8 g, m.p. of 113°–115° C. (80% of theory).

Theory for $C_{43}H_{66}N_4SbF_6$:
Theory %C=58.48; %H=7.60; %N=6.40; %F=13.22
Found %C=57.97; %H=7.81; %N=5.94; %F=10.66

2. Conversion Of Monovalent Salt To Divalent Salt 15.0 g (0.02 mole) of tris-di-n-butylaminophenyl aminium hexafluoroantimonate in 100 ml of acetone is treated with 3.4 g (0.02 mole) of silver nitrate and 10.4 g (0.04 mole) of sodium hexafluoroantimonate in 100 ml of acetone. The mixture is stirred at 50° C. for 3 hours and filtered to removed precipitated silver metal. This is washed with 50 ml of warmed acetone and the filtrates combined. Water, about 150 ml, is added to this solution. A green precipitate forms which is thoroughly washed with water, then isopropanol and dried. It weighs 20.6 g (92% of theory). The crude sample had a m.p. of 190°–193° C.

EXAMPLE 8

N,N-diethyl-N',N'-bis(diethylaminophenyl)-p-benzoquinone diimmonium hexafluoroantimonate

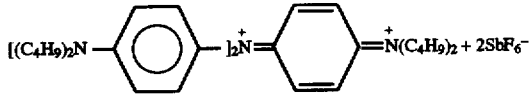

(a) From a Free Base

To a solution of 9.16 g (0.02 moles) of tris p-diethylaminophenyl amine in 40 ml of tetrahydrofuran, there is added 6.8 g (0.04 mole) of silver nitrate and 20.70 g (0.08 mole) of sodium hexafluoroantimonate. The mixture is stirred at 40°–45° C. for 2 hours and the precipitated silver is removed by filtration and washed with 40 ml of tetrahydrofuran. The washings are added to the filtrate and 80 ml of water is added slowly, over one hour with stirring. A dark green precipitate forms which is collected, washed with water and dried. It weighs 16.5 g (88.5% of theory) and melts at 147°–148.5° C.

Theory for $C_{30}H_{42}N_4Sb_2F_{12}$:
Theory %C=38.73; %H=4.52; %N=6.03; %F=24.53
Found %C=38.99; %H=4.72; %N=6.05; %F=23.10

(b) From the Monovalent Salt:

1. Preparation Of Monovalent Salt

The monovalent salt is prepared in a manner similar to that described in Example 7. It had the same physical constants as the product described in U.S. Pat. No. 3,341,464. A 9.46 g (0.02 mole) sample is dissolved in 150 ml of acetone and treated with 3.4 g (0.02 mole) of silver nitrate and 10.4 g (0.04 mole) of sodium hexafluoroantimonate in 100 ml of acetone. The mixture is stirred overnight at 40° C. and the silver metal removed by filtration. It is washed with 50 ml of warm acetone and the filtrates combined. The addition of 200 ml of water gives a green crystalline precipitate. This is washed and dried. It weighs 13.7 g (97.9% of theory) and has the same melting point as the product made from the free base.

EXAMPLE 9

The dicationic dyes extend absorption maxima down to lower wavelengths and absorbs a broader range of wavelengths in the near infrared. Table I shows the effect of structure on these characteristics. The structures compared are for each dye in the family:

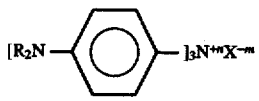

TABLE I

| R | Anion | n | Absorption Maxima Range (nm) | Transmission in* Visible (%) |
|---|---|---|---|---|
| $C_4H_9$ | $PF_6$ | 2 | 720 to 1030 | 96 |
| $C_4H_9$ | $PF_6$ | 1 | 780 to 1100 | 95 |
| $C_4H_9$ | $SbF_6$ | 2 | 800 to 925 | 84 |
| $C_4H_9$ | $SbF_6$ | 1 | 990 | 83 |
| $C_2H_5$ | $SbF_6$ | 2 | 900 to 980 | 100 |
| $C_2H_5$ | $SbF_6$ | 1 | 930 (sharp) | 100 |
| $C_2H_5$ | $PF_6$ | 2 | 780 to 925 | 99 |
| $C_2H_5$ | $PF_6$ | 1 | 975 | 100 |

*Concentrations are approximately 1.5 mg/100 ml of acetone.

What is claimed is:

1. The invention provides a near IR dye of the formula I:

(I)

wherein:

R=$C_1$ to $C_6$ alkyl;

Ar=divalent phenyl which may or may not be ring substituted with one or more alkyl, alkoxy, halogen, nitro, cyano or carboalkoxy groups;

Ar'=quinoidal phenyl which may or may not be ring substituted with one or more alkyl, alkoxy, halogen, nitro, cyano or carboalkoxy groups; and X=an anion of a strong acid.

2. The near IR dye compound of claim 1 wherein X is an anion selected from the group consisting of tetrafluoroborate, hexafluoroarsenate, hexafluorophosphate, hexafluoroaluminate, hexafluorosilicate, hexafluoroantimonate and perchlorate.

3. A method of preparing a compound of the formula I:

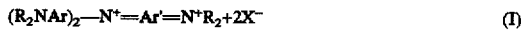
(I)

which comprises double oxidizing a compound of the formula II:

(II)

wherein:

R=$C1$-$C_6$ alkyl;

Ar=divalent phenyl which may or may not be ring substituted with one or more alkyl, alkoxy, halogen, nitro, cyano or carboalkoxy groups;

Ar'=quinoidal phenyl which may or may not be ring substituted with one or more alkyl, alkoxy, halogen, nitro, cyano or carboalkoxy groups; and X=is an anion of a strong acid;

wherein the oxidizing is conducted in the presence of an oxidant selected from the group consisting of silver salts and copper salts and a component having an anion of a strong acid.

4. The method of claim 3 wherein the double oxidizing is conducted with a component having an anion of a strong acid which is selected from the group consisting of a tetrafluoroborate, hexafluoroarsenate, hexafluorophosphate, hexafluoroaluminate, hexafluorosilicate, hexafluoroantimonate and perchlorate.

5. The method of claim 3 wherein the double oxidizing is conducted with an oxidant having the formula MZ or $MZ_2$ wherein M is silver or copper and Z is an anion selected from the group consisting of nitrate, chloride, bromide, sulfate and acetate.

6. A near IR dye compound of the formula IV:

(IV)

wherein:

R=$C_1$-$C_6$ alkyl;

Ar=divalent phenyl which may or may not be ring substituted with one or more alkyl, alkoxy, halogen, nitro, cyano or carboalkoxy groups.

* * * * *